United States Patent [19]

Imada et al.

[11] Patent Number: 5,630,804
[45] Date of Patent: May 20, 1997

[54] METALLIC SILVER-PLATED SILICON RING ELEMENT FOR EXIT SITE DISINFECTION AND A METHOD FOR PREVENTING CONTAMINATION AT AN EXIT SITE

[75] Inventors: Akio Imada, Osaka; Tatsumichi Takeda, Tokyo, both of Japan

[73] Assignee: Baxter International Inc., Deerfield, Ill.

[21] Appl. No.: 394,685

[22] Filed: Feb. 24, 1995

[51] Int. Cl.$^6$ ................................................ A61M 25/00
[52] U.S. Cl. ...................... 604/265; 604/905; 604/29; 604/283; 604/20; 128/912
[58] Field of Search ............................. 604/264–266, 604/280, 283, 284, 19–22, 174, 29, 905; 128/912

[56] References Cited

U.S. PATENT DOCUMENTS

| | | | |
|---|---|---|---|
| 4,054,139 | 10/1977 | Crossley | 604/265 X |
| 4,569,673 | 2/1986 | Tesi | 604/20 |
| 4,581,028 | 4/1986 | Fox, Jr. et al. | 604/265 X |
| 4,776,349 | 10/1988 | Nashef et al. | 604/21 X |
| 4,814,231 | 3/1989 | Onohara et al. | 604/265 X |
| 4,838,876 | 6/1989 | Wong et al. | 604/265 |
| 5,049,140 | 9/1991 | Brenner et al. | 604/265 X |
| 5,053,003 | 10/1991 | Dadson et al. | 604/283 |
| 5,236,422 | 8/1993 | Eplett, Jr. | |
| 5,295,979 | 3/1994 | DeLaurentis et al. | 604/265 |
| 5,308,338 | 5/1994 | Helfrich | |
| 5,324,275 | 6/1994 | Raad et al. | 604/265 |
| 5,360,397 | 11/1994 | Pinchuk | 604/266 |
| 5,380,298 | 1/1995 | Zabetakis et al. | 604/265 |
| 5,403,295 | 4/1995 | Byrne et al. | 604/265 |
| 5,498,248 | 3/1996 | Milder | 604/265 |
| 5,527,281 | 6/1996 | Haas | 604/283 |

FOREIGN PATENT DOCUMENTS

| | | | |
|---|---|---|---|
| 0183396 | 6/1986 | European Pat. Off. | 604/283 |
| 2720776 | 11/1978 | Germany. | |
| 4115390A1 | 5/1991 | Germany. | |
| 93/17747 | 9/1993 | WIPO | 604/283 |

Primary Examiner—Michael Powell Buiz
Assistant Examiner—Chalin Smith
Attorney, Agent, or Firm—Thomas S. Borecki; Charles R. Mattenson; Robert M. Barrett

[57] ABSTRACT

A ring element (10) attaches to a length of tubing (12) to prevent contamination at a site (24) through which a portion of the length of tubing (12) extends. A resilient material having a first end (14) and a second end (16) is provided capable of mating to form a hollow, cylindrical shell (10). An electrically conductive material is provided on a surface of the resilient material. In a preferred embodiment, the conductive material includes silver. The ring element (10) may be placed on a tube (12) to prevent contamination at a site (24) through which a tube (12) is secured. The ring element (10) is connected to the tube (12) at the site (24) of injection of the tube (12) wherein the ring element (10) is capable of removal without removal of the tube (12) from the site (24). The ring element (10) is particularly adaptable for a transfer set connectable to a peritoneal cavity and insertable at a site (24) for, for example, peritoneal dialysis.

15 Claims, 1 Drawing Sheet

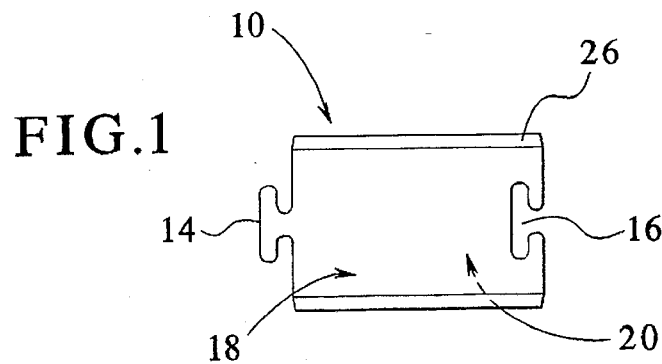
FIG. 1
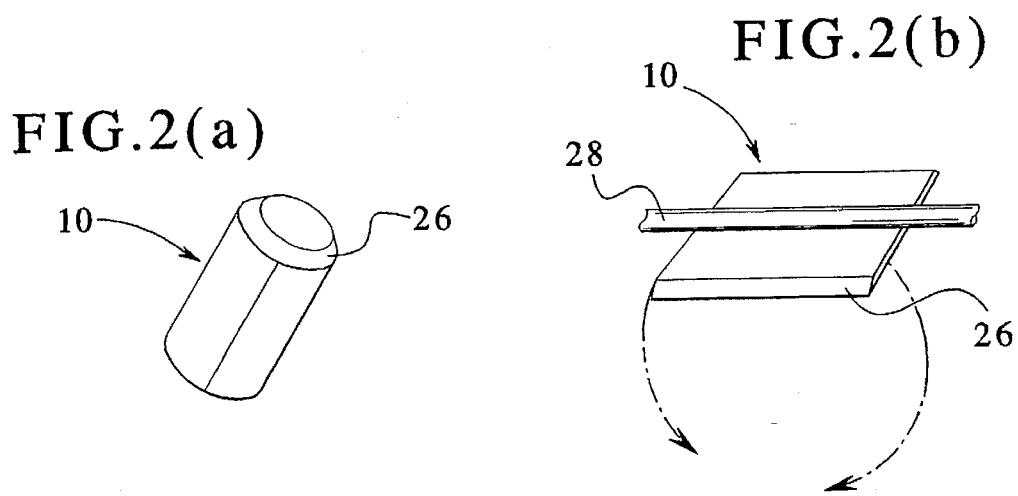
FIG. 2(a)
FIG. 2(b)
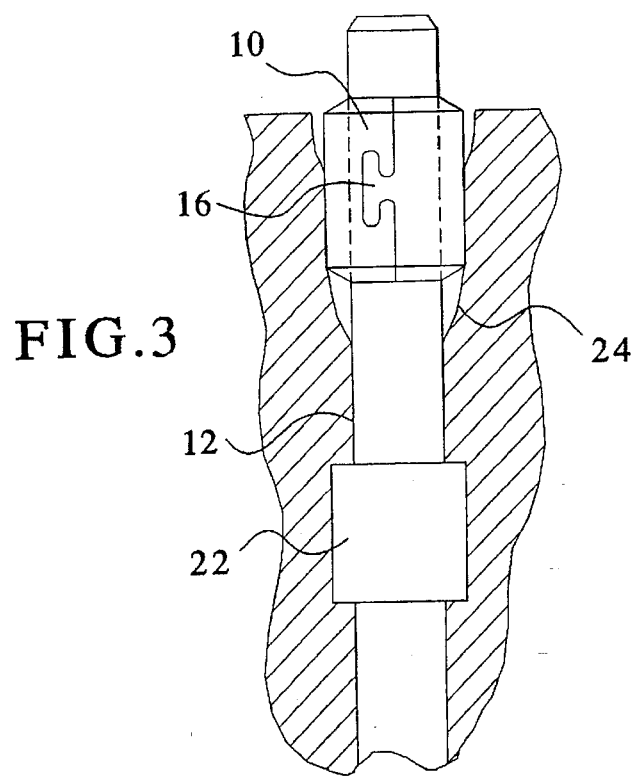
FIG. 3

METALLIC SILVER-PLATED SILICON RING ELEMENT FOR EXIT SITE DISINFECTION AND A METHOD FOR PREVENTING CONTAMINATION AT AN EXIT SITE

BACKGROUND OF THE INVENTION

The present invention generally relates to prevention of microorganism invasion and disinfection at an exit site of, for example, a catheter placed into a cavity of a body of an individual. More specifically, the present invention relates to a metallic silver-plated silicon ring element for disinfection of an exit site and prevention of microorganism invasion into cuffs of a catheter and a tunnel formed by the catheter using oligodynamic effect of the silver ion of the ring element.

It is, of course, generally known to maintain sterile conditions when articles, such as a catheter, are inserted into a cavity of the body. One such procedure requiring insertion of a catheter into the body creating an entry/exit site is peritoneal dialysis. At the point of insertion, an entry/exit site is created for the catheter or other like tubular device to permit injection or withdrawal of fluid into the cavity or to establish patency of the passageway.

Many techniques are known to maintain the sterility or cleanliness of the entry/exit site. One such technique requires daily care of the site by a disinfectant such as PVI, chlorhexidine, or the like. The procedure, however, only provides immediate disinfection. It is difficult to maintain a clean environment at all times by only using a disinfectant.

Another known procedure is to cover the site by a plastic bag or an adhesive material capping. However, many allergic problems result from using adhesive material. Further, no disinfection of the site results from use of the plastic bag or adhesive material capping. Using a disinfectant such as PVI, however, often causes skin irritation since PVI is caustic and can result in inflammation at the site.

Another known technique involves using a silver coated catheter. Such a catheter may be chronic and a silver ion used as the coating with the catheter may react with sulphur-containing substances or iodine-containing substances. Therefore, less leaching of the silver ions from the silver layer results. Peritonitis is increasingly occurrent at the site created through the use of catheters. Infections caused through peritonitis are both difficult and slow to heal. Therefore, catheter re-implantation into the body is often required. Often, a patient ends continuous ambulatory peritoneal dialysis (CAPD) therapy due to the complications caused by peritonitis and other like infections.

A need, therefore, exists for an improved apparatus and a method for eliminating infections due to implantation of a catheter and the like.

SUMMARY OF THE INVENTION

The present invention provides a ring element for attachment to a length of tubing to prevent contamination at a site through which a portion of the length of tubing extends. Further, the present invention provides a method for preventing contamination at a site through which a tube is secured.

To this end, in an embodiment, the present invention provides a ring element for attachment to a length of tubing to prevent contamination of a site through which a portion of the length of tubing extends. The ring element has a resilient material having a first end and a second end capable of mating to form a hollow, cylindrical shell. An electrically conductive material is provided on a surface of the resilient material.

In an embodiment, the electrically conductive material of the ring element includes silver.

In an embodiment, the resilient material of the ring element includes silicon.

In an embodiment, the electrically conductive material of the ring element is sputtered on the surface of the resilient material.

In an embodiment, the electrically conductive material of the ring element is impregnated in the resilient material.

In an embodiment, the ring element has a male component at the first end of the resilient material and a female component at the second end of the resilient material wherein the male component is removably attachable to the female component.

In an embodiment, the ring element has a chamfered edge on a downstream side of the hollow, cylindrical shell formed by the resilient material.

In an embodiment, the ring element has an electrically conductive wire operatively connected to the resilient material.

In another embodiment of the present invention, a method is provided for preventing contamination at a site through which a tube is secured. The method comprises the steps of: providing a ring element having an electrically conductive material; and connecting the ring element to the tube at the site, the ring element capable of removal without removal of the tube from the site.

In an embodiment, the method further comprises the step of providing an electrically conductive wire operatively connected to the ring element. The method may provide current through the wire provoking an oligodynamic action at the site.

In an embodiment, the method further comprises the step of removing the ring element from the tube.

In an embodiment, the method further comprises the step of forming the ring element by connecting a female portion to a male portion at opposite ends of the ring element.

In an embodiment, the method further comprises the step of securing the tube at the site wherein the ring element is constructed and arranged at the site.

In another embodiment of the present invention, a transfer set is connectable to a peritoneal cavity and insertable at a site. The transfer set has a length of tubing, an element removably securable around a portion of the length of tubing and an electrically conductive agent constructed and arranged on the element and capable of releasing the agent at the site thereby preventing contamination at the site.

In an embodiment, the transfer set has electrically conductive wires secured to the element and connectable to a source capable of providing current to the element to assist in release of the agent. In an embodiment, the transfer set has a female component and a male component at opposite ends of the element, the female component engageable with the male component to form a ring.

It is, therefore, an advantage of the present invention to provide a ring element, a method and a transfer set that prevents contamination at a site through which a portion of a length of tubing extends.

Another advantage of the present invention is to provide a removable ring element to prevent contamination at a site through which a portion of a length of tubing extends.

A still further advantage of the present invention is to provide a simple ring element and a method for preventing contamination at a site through which a portion of a length of tubing extends.

And, a further advantage of the present invention is to provide a low-cost element and a method for preventing contamination at a site through which a portion of a length of tubing extends.

Additional features and advantages of the present invention are described in, and will be apparent from, the detailed description of the presently preferred embodiments and from the drawings.

BRIEF DESCRIPTION OF THE DRAWINGS

FIG. 1 illustrates a plan view of an embodiment of a ring element of the present invention prior to formation of the ring.

FIG. 2(a) illustrates a perspective view of an embodiment of the ring element following formation into its cylindrical shape.

FIG. 2(b) illustrates a plan view of an embodiment of a ring element of the present invention prior to formation into its cylindrical shape.

FIG. 3 illustrates a plan view of an embodiment of a ring element of the present invention secured around a catheter or other like tubing.

DETAILED DESCRIPTION OF THE PRESENTLY PREFERRED EMBODIMENTS

The present invention provides a system and a method to prevent invasion of microorganisms into the catheter cuffs and into the tunnel created by the catheter. To this end, the present invention provides a system and a method which uses the oligodynamic effect of silver ions to prevent microorganism invasion and/or like infection.

The system provides an element coated or otherwise impregnated with metallic silver and is placed on a CAPD catheter on its track at all times. The element is capable of releasing a silver ion in trace amounts during wet conditions and may be changed at regular periods providing a fresh surface for ion release. The coating of the element is performed by an ion vapor deposition method that controls the ratio of crystal/amorphous and surfacial lattice of silver crystals.

The coat is electrically conductive material, preferably metallic silver, on silicon material. Controlled silver ion release from the ring element may be effected by a weak electric direct current and, if necessary, heat. The base material consists of a silicon material similar to the Young's modulus of human tissue. The design of the element is substantially cylindrical with an open cut that simplifies coating of an inner layer as well as simplifies exchange on the CAPD catheter with no disconnection step required of a distal end of the catheter and/or a catheter adapter/transfer set. To this end, the design may implement a hook and butt combination that maintains the ring element in smooth and tight contact to the CAPD catheter.

Referring now to the drawings wherein like numerals refer to like parts, FIG. 1 generally illustrates a metallic silver-plated silicon ring element 10 of the present invention. The ring element 10 may be coated with silver by silver sputtering on one or both sides of the ring element 10. The base material of the ring element 10 includes silicon forming a material having a Young's modulus similar to that of human tissue.

The coating of the surface of the ring element 10 may be performed by an ion vapor deposition method as is well-known in the art. This method controls the ratio of crystal/amorphous and surfacial lattice of silver crystals.

The ring element 10, due to the elasticity in the silicon base material, is capable of bending from its flat shape, as illustrated in FIG. 1, to a ring-like element that is designed to be secured around an outside wall of, for example, a CAPD catheter 12 as illustrated in FIG. 3. When the ring element 10 is placed on the CAPD catheter 12, a male portion 14, in a preferred embodiment, is insertable into a female portion 16 at opposite ends of the ring element 10. The design of the ring element 10 provides a cylindrical interior surface that maintains both a smooth and tight contact to the catheter 12.

Both surfaces, a top surface 18 and a bottom surface 20, of the ring element 10 may be coated with metallic silver or otherwise impregnated with metallic silver or other electrically conductive material on the silicon material. A controlled silver ion release may be effected by a weak electric direct current and, if necessary, heat.

The design of the ring element 10 allows the ring element 10 to be removed from the catheter 12 without disconnection of the catheter 12 and/or the catheter adapter/transfer set attached to, for example, a patient.

The ring element 10 prevents invasion of microorganisms into, for example, a cuff 22 of the catheter 12 or a tunnel created at an exit site 24 or the point of entry/exit of the catheter 12 into, for example, human tissues at a point or site required to conduct, for example, peritoneal dialysis administration to a patient.

Referring now to FIG. 2(a), another embodiment of a ring element 10' is generally illustrated. The ring element 10', in a preferred embodiment, includes a chamfer 26 at its distal end such that insertion of the ring element 10' at the entry/exit site 24 may be effected without irritation at the entry/exit site.

FIG. 2(b) illustrates an embodiment of the ring element 10' in its flat position prior to forming the ring for securing onto, for example, the catheter 12. The ring element 10' may include electrically conductive wire 28 through which a current may be supplied to effect controlled agent release of silver with the electric current. Multiple wires may be attached to the ring element 10' to assist in release of the silver with the assistance of application of current from a current source (not shown) through the wire.

In a preferred embodiment, the male portion 14 and the female portion 16 are implemented to secure the ring element 10 in its shape for securing around the catheter 12. Other known arrangements for effecting a ring element from a flat piece to a cylindrical ring that may be simply attached and removed from a tubular structure, such as the catheter 12, may be implemented by those skilled in the art.

In a preferred embodiment, as previously set forth, the silicon material has a Young's modulus of elasticity similar to human skin or tissue. The length, in a preferred embodiment, is between five and twenty millimeters and is designed to be disposable after a single use, if desired. A new ring element 10 may be secured around the catheter 12 following disposal of a used ring element 10.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A ring element for attachment to a length of tubing to prevent contamination at a site through which a portion of the length of tubing extends, the ring element comprising:

a resilient, silicon-based material having a first end and a second end capable of mating to form a hollow cylindrical shell;

an electrically conductive material on a surface of the resilient, silicon-based material;

a male component at the first end of the resilient, silicon-based material; and a female component at the second end of the resilient, silicon-based material wherein the male component is removably attachable from the female component and further wherein the male component and the female component form a single, non-overlapping layer and continuous connection after insertion of the male component with the female component.

2. The ring element of claim 1 wherein the electrically conductive material includes silver.

3. The ring element of claim 1 wherein the surface of the resilient, silicon-based material includes impregnated electrically conductive material.

4. The ring element of claim 1 wherein the resilient, silicon-based material includes impregnated electrically conductive material.

5. The ring element of claim 1 further comprising:

a chamfered edge on a downstream side of the hollow, cylindrical shell formed by the resilient material.

6. The ring element of claim 1 further comprising:

electrically conductive wire operatively connected to the resilient material.

7. A method for preventing contamination at a site through which a tube is secured, the method comprising the steps of:

providing only a single ring element formed from a silicon-based material having an electrically conductive material;

connecting only the single ring element to the tube at the site, the ring element capable of removal without removal of the rube from the site; and forming the single ring element by connecting a female portion to a male portion at opposite ends of the single ring element wherein the male portion and the female portion provide a single, non-overlapping layer and continuous connection.

8. The method of claim 7 wherein the electrically conductive material includes silver.

9. The method of claim 7 further comprising the step of:

removing the ring element from the tube.

10. The method of claim 7 further comprising the step of:

securing the tube at the site wherein the ring element is constructed and arranged at the site.

11. The method of claim 7 further comprising the step of:

providing an electrically conductive wire operatively connected to the ring element.

12. The method of claim 11 further comprising the step of:

providing current through the wire provoking an oligodynamic action at the site.

13. A transfer set connectable to a peritoneal cavity and insertable at a site, the transfer set comprising:

a length of tubing;

an element formed from a silicon-based material removably securable around a portion of the length of tubing wherein only a single element is secured around the portion of the length of tubing;

an electrically conductive agent constructed and arranged on the element and capable of releasing the agent at the site thereby preventing contamination at the site; and a female component and a male component at opposite ends of the element, the female component engageable with the male component to form a single, non-overlapping layer and continuous ring.

14. The transfer set of claim 13 wherein the electrically conductive agent includes silver.

15. The transfer set of claim 13 further comprising:

electrically conductive wire secured to the element and connectable to a source capable of providing current to the element to assist in release of the agent.

* * * * *

UNITED STATES PATENT AND TRADEMARK OFFICE
CERTIFICATE OF CORRECTION

PATENT NO. : 5,630,804

DATED : May 20, 1997

INVENTOR(S) : Akio Imada and Tatsumichi Takeda

It is certified that error appears in the above-identified patent and that said Letters Patent is hereby corrected as shown below:

Column 5, Line 37: delete "rube" and insert --tube--

Signed and Sealed this

Second Day of December, 1997

Attest:

BRUCE LEHMAN

*Attesting Officer*  *Commissioner of Patents and Trademarks*